(12) United States Patent
Kabanov et al.

(10) Patent No.: US 7,422,875 B2
(45) Date of Patent: Sep. 9, 2008

(54) COMPOSITIONS AND METHODS FOR INCREASING PROTEIN PRODUCTION

(75) Inventors: Alexander V. Kabanov, Omaha, NE (US); Valery Alakhov, Baie d'Urfe (CA)

(73) Assignee: Board of Regents of the University of Nebraska, Omaha, NE (US)

( * ) Notice: Subject to any disclaimer, the term of this patent is extended or adjusted under 35 U.S.C. 154(b) by 458 days.

(21) Appl. No.: 10/894,709

(22) Filed: Jul. 20, 2004

(65) Prior Publication Data

US 2006/0019257 A1 Jan. 26, 2006

(51) Int. Cl.
*C12P 21/07* (2006.01)
(52) U.S. Cl. ...................... 435/69.1; 435/455
(58) Field of Classification Search ........................ None
See application file for complete search history.

(56) References Cited

U.S. PATENT DOCUMENTS

| | | | |
|---|---|---|---|
| 5,024,947 A * | 6/1991 | Inlow et al. ................. | 435/404 |
| 5,656,611 A | 8/1997 | Kabanov | |
| 5,804,420 A | 9/1998 | Chan | |
| 6,221,959 B1 | 4/2001 | Kabanov | |
| 6,277,410 B1 | 8/2001 | Kabanov | |
| 6,353,055 B1 | 3/2002 | Kabanov | |
| 6,359,054 B1 | 3/2002 | Lemieux | |
| 6,440,743 B1 | 8/2002 | Kabanov | |
| 6,599,724 B1 | 7/2003 | Mikaelsson | |
| 2002/0019358 A1 | 2/2002 | Manthrope | |

OTHER PUBLICATIONS

Sriadibhatla, S., et al. "Enhancement of Gene Expression in Stably Transfected Cells by Amphiphilic Block Copolymers" JACS, Jan. 16, 2004.

Gebhart, C, et al. "Pluronic Block Copolymers in Gene Delivery" Presented at Controlled Release Society, 30th Annual Meeting, Glasgow, Scotland, U.K. Jul. 21, 2003.

Astafieva, I., et al. Enhancement of the Polycation-Mediated DNA Uptake and Cell Transfection with Pluronic P85 Block Copolymer. FEBS Letters 389 (1996) 278-280.

Nguyen, H-K, et al. "Evaluation of Polyether-Polyethyleneimine Graft Copolymers as Gene Transfer Agents" Gene Therapy (2000) 7, 126-138.

Gebhart, C., et al. Design and Formulation of Polyplexes Based on Pluronic-Polyethyleneimine Conjugates for Gene Transfer Bioconjugate Chem. (2002) 13, 937-944.

Kabanov, A., et al. Pluronic Block Copolymers: Novel Functional Molecules for Gene Therapy Advanced Drug Delivery Reviews (2002) 54 223-233.

Kabanov, A., et al. "Polymer Genomics: Shifting the Gene and Drug Delivery Paradigms" Paper presented at the 8th European Symposium on Controlled Drug Delivery, Apr. 7-9, 2004, Noordwijk Aan Zee, The Netherlands.

Kabanov, A., et al. "Polymer Genomics: Shifting the Gene and Drug Delivery Paradigms" Journal of Controlled Release (2005) 101 259-271.

Lemieux, P., et al. "A Combination of Poloxamers Increases Gene Expression of Plasmid DNA in Skeletal Muscle" Gene Therapy (2000) 7, 986-991.

Alakhov, V. "Block Copolymeric Biotransport Carriers as Versatile Vehicles for Durg Delivery" Expert Opin. Biol. Ther. (2001) 1 (4) 583-602.

\* cited by examiner

*Primary Examiner*—James S Ketter
(74) *Attorney, Agent, or Firm*—Dann, Dorfman, Herrell and Skillman; Kathleen D. Rigaut; Robert C. Netter, Jr.

(57) ABSTRACT

Compositions and methods for increasing protein production are provided.

27 Claims, 10 Drawing Sheets

COMPOSITIONS AND METHODS FOR INCREASING PROTEIN PRODUCTION

FIELD OF THE INVENTION

The present invention relates to methods for increasing protein and RNA production.

BACKGROUND OF THE INVENTION

Several publications and patent documents are cited throughout the specification in order to describe the state of the art to which this invention pertains. Each of these citations is incorporated herein by reference as though set forth in full.

Non-viral gene delivery is a critically important method of delivering genes to a cell both in vitro and in vivo. To enhance the transfer of DNA into the cells, polycations and polymer agents have been employed that can 1) bind and condense DNA, 2) protect the DNA from degradation, and 3) enhance transport of the DNA into the cell (Wagner et al. (1990) PNAS, 87:3410-3414; Kabanov et al. (1993) Bioconj. Chem., 4:448-454; Boussif et al. (1995) PNAS, 92:7297-7301; Tang et al. (1997) Gene Ther., 4:823-832; Pollard et al. (1998) J. Biol. Chem., 273:7507-7511; Godbey et al. (1999) PNAS, 96:5177-5181; Merdan et al. (2002) Pharm. Res., 19:140-146). Amphiphilic block copolymers have been employed to increase the transfer of naked DNA in vivo into a variety of tissues including muscle and skin tissues and tumors (Lemieux et al. (2000) Gene Ther., 7:986-991; Liaw et al. (2001) Gene Ther., 8:999-1004; Alakhov et al. (2001) Expert Opin. Biol. Ther., 1:583-602; Gebhart et al. (2003) Controlled Release Society, Glasgow, Scotland, UK; Pitard et al. (2002) Human Gene Ther., 13:1767-1775; Batrakova et al. (2003) J. Pharmacol. Exp. Ther., 304:845-854). Additionally, amphiphilic block copolymers have been shown to increase the transfer of polycation-DNA complexes (Nguyen et al. (2000) Gene Ther., 7:126-138; Gebhart et al. (2002) Bioconj. Chem., 13:937-944; Astafieva et al. (1996) FEBS Lett., 389: 278-280; Kuo, J. H. (2003) Biotechnol. Appl. Biochem., 37:267-271).

Transduction of cells with viral vectors, such as adenoviral and lentiviral, is also increased in the presence of amphiphilic block copolymers (March et al. (1995) Hum. Gene Ther., 6:41-53; Feldman et al. (1997) Gene Ther., 4:189-198; Van Belle et al. (1998) Hum. Gene Ther., 9:1013-1024; Maillard et al. (2000) Gene Ther., 7:1353-1361; Dishart et al. (2003) J. Mol. Cell. Cardiol., 35:739-748).

All of the above studies demonstrate the ability of amphiphilic block copolymers to assist in the transfer of DNA and DNA-containing compositions into cells. However, such studies are silent as to the effect of the polymers on gene expression of genes already present in the cell.

SUMMARY OF THE INVENTION

The present invention broadly relates to compositions and methods for increasing gene expression and protein yield.

According to one aspect of the invention, a method for producing a protein is provided comprising the steps of 1) providing cells comprising a heterologous nucleic acid encoding a recombinant protein and 2) incubating the cells in media containing at least one amphiphilic block copolymer. The cells may be maintained in the media containing at least one amphiphilic block copolymer or be removed to media which does not contain amphiphilic block copolymers.

According to another aspect of the instant invention, the protein produced by the methods of the instant invention may be isolated.

In accordance with another aspect of the instant invention, the amphiphilic polymer employed in the instant methods is a copolymer comprising at least one block of poly(oxyethylene) and at least one block of poly(oxypropylene).

According to another aspect of the instant invention, the amphiphilic block copolymer of the instant method is a mixture of at least two different amphiphilic block copolymers. For example, the mixture can comprise, without limitation, Pluronic® P123 and Pluronic® P127, or Pluronic® P85 and Pluronic® F88.

In still another embodiment of the instant invention, the amphiphilic block copolymer of the instant methods is a mixture of a Pluronic® copolymer and a polycation conjugated Pluronic® copolymer. In a preferred embodiment, the mixture comprises Pluronic® P123 and Pluronic® P123 conjugated to polyethyleneimine. According to another aspect of the invention, the cells are incubated in media comprising at least one amphiphilic block copolymer for at least three hours. In a particular embodiment, the cells are incubated for at least nine hours in media comprising at least one amphiphilic block copolymer.

According to another aspect of the invention, the heterologous nucleic acid is stably incorporated into said cells.

In still another embodiment of the invention, a method for producing a protein in a host is provided comprising the steps of 1) providing a cell comprising a heterologous nucleic acid encoding a recombinant protein, 2) incubating the cells in media containing at least one amphiphilic block copolymer, and 3) introducing the cells into a host. In a particular embodiment, the cells are originally obtained from the host and the heterologous nucleic acid is incorporated into the cells in vitro.

In another embodiment of the instant invention, a method is provided for enhancing production an RNA comprising the steps of 1) providing cells comprising a heterologous DNA encoding an RNA; and 2) incubating the cells in media containing at least one-amphiphilic block copolymer. In a particular embodiment, the encoded for RNA is an siRNA.

In yet another embodiment of the invention, a composition is provided comprising stably transformed cells, at least one amphiphilic block copolymer, and nucleic acid free media.

In yet a further aspect of the invention, kits are provided for performing the methods described above. Such kits comprise an amphiphilic block polymer, reagents to transform a cell, and a selection agent to isolate stably transformed cells. The kits may further comprise frozen stocks of host cells.

BRIEF DESCRIPTIONS OF THE DRAWING

FIG. 1 is a graph of the luciferase present in Luc-NIH3T3 cells treated with media alone or media containing 0.03%, 0.1%, or 0.3% Pluronic® P85. The data is reported as mean ± standard deviation (SD) (n=3). The statistical significance of treated versus control samples is shown, (*)=p<0.05 and (**) =p<0.005.

Figure 4:
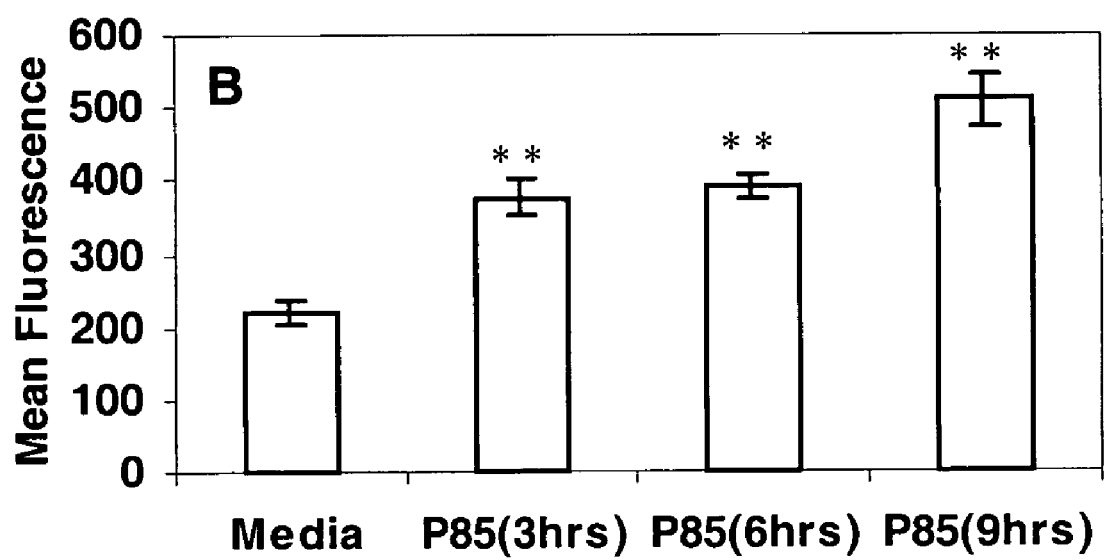

FIG. 4 is a graph of the fluorescence of cells treated with media alone or with 0.1% Pluronic® P85 for 3, 6, or 9 hours. The data is reported as mean ± SD (n=3). The statistical significance of treated versus control samples is shown, (**) =p<0.005.

Figure 5A:
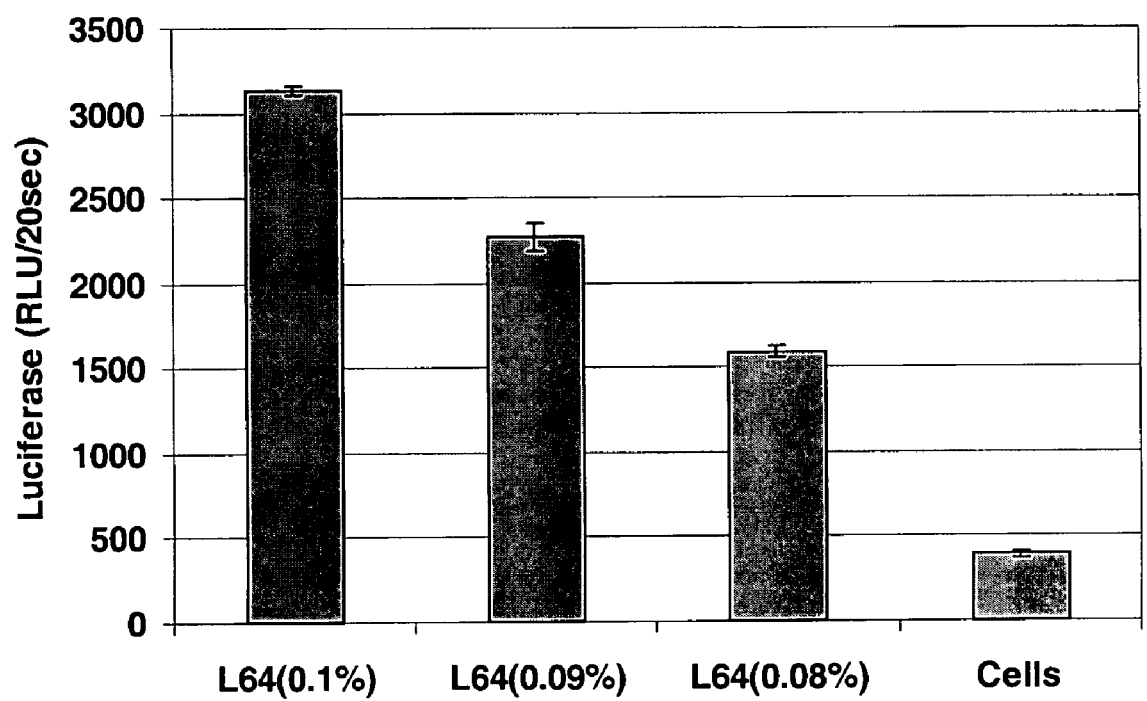
Figure 5B:
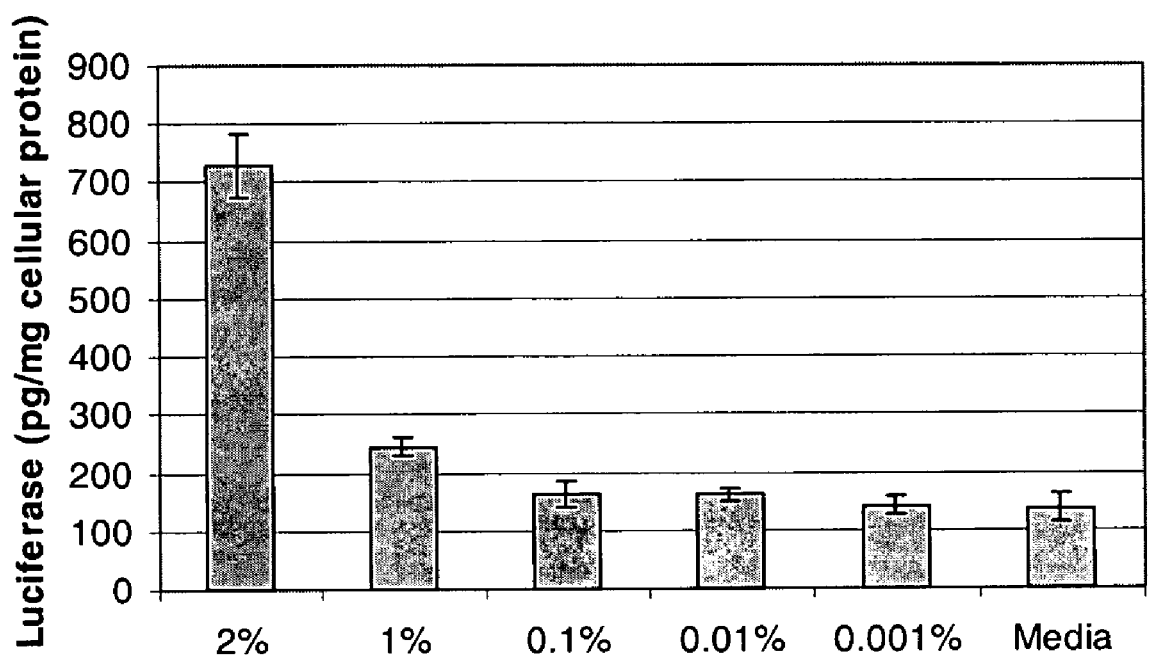
Figure 5C:
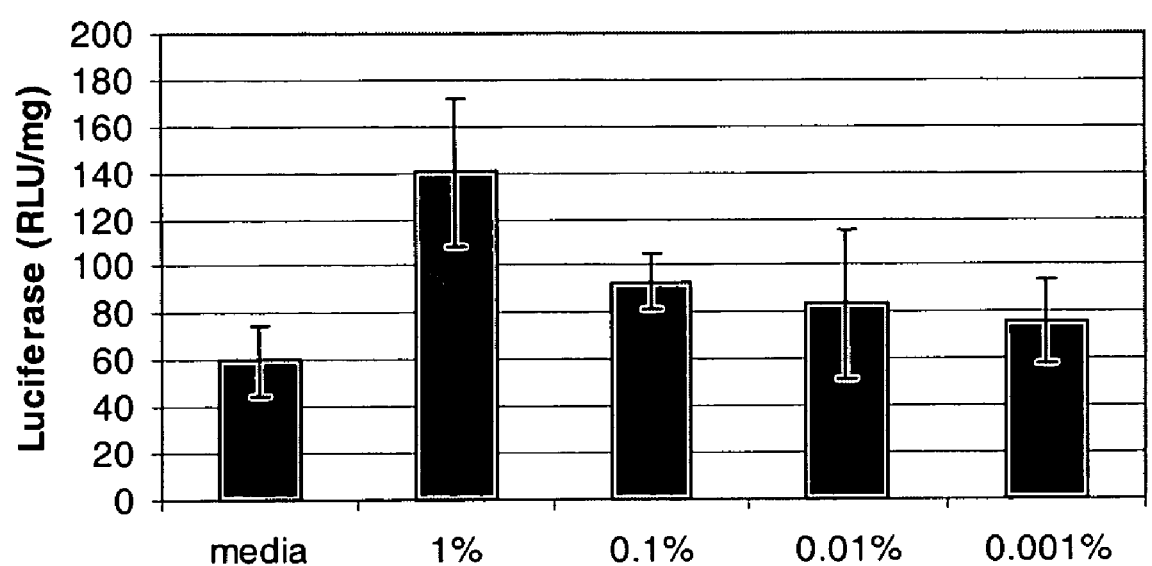
Figure 5D:
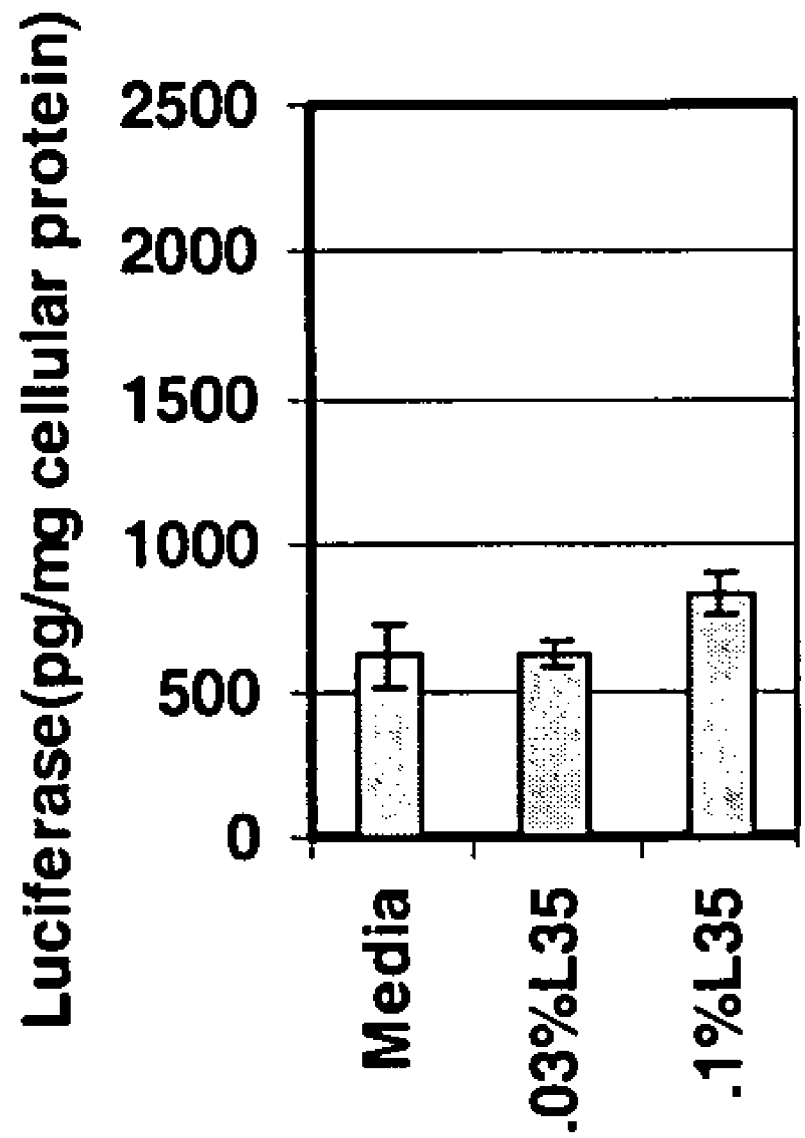

FIG. 5A is a graph of the luciferase present in Luc-NIH3T3 cells treated with media alone or media containing 0.08%, 0.09%, or 0.1% Pluronic® L64. FIG. 5B is a graph of the luciferase per mg of cellular protein present in Luc-NIH3T3 cells treated with media alone or media containing 0.001%, 0.01%, 0.1%, 1%, or 2% Pluronic® P123. FIG. 5C is a graph of the luciferase present in Luc-NIH3T3 cells treated with media alone or media containing 0.001%, 0.01%, 0.1%, or 1% of a 1:8 mixture of Pluronic® L61 and Pluronic® F127. FIG. 5D is a graph of the luciferase present per mg of cellular protein in Luc-NIH3T3 cells treated with media alone or media containing 0.03% or 0.1% Pluronic® L35. The data are reported as mean ± SD (n=3).

Figure 6A:
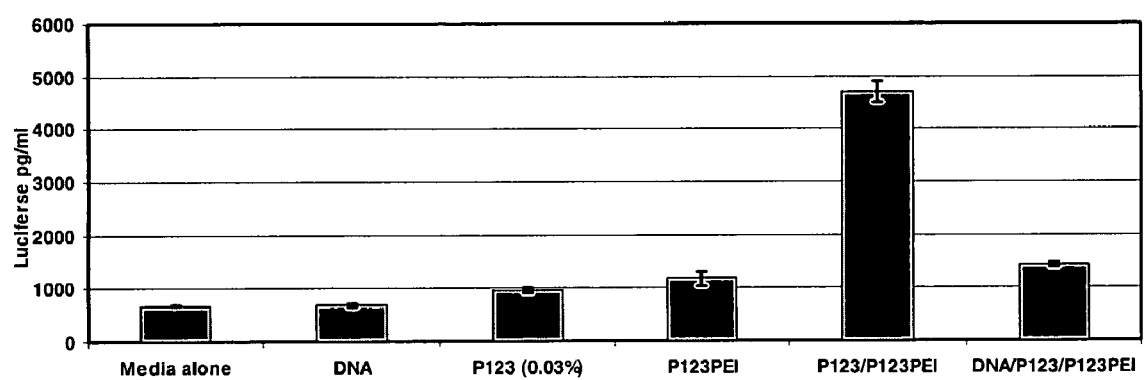
Figure 6B:
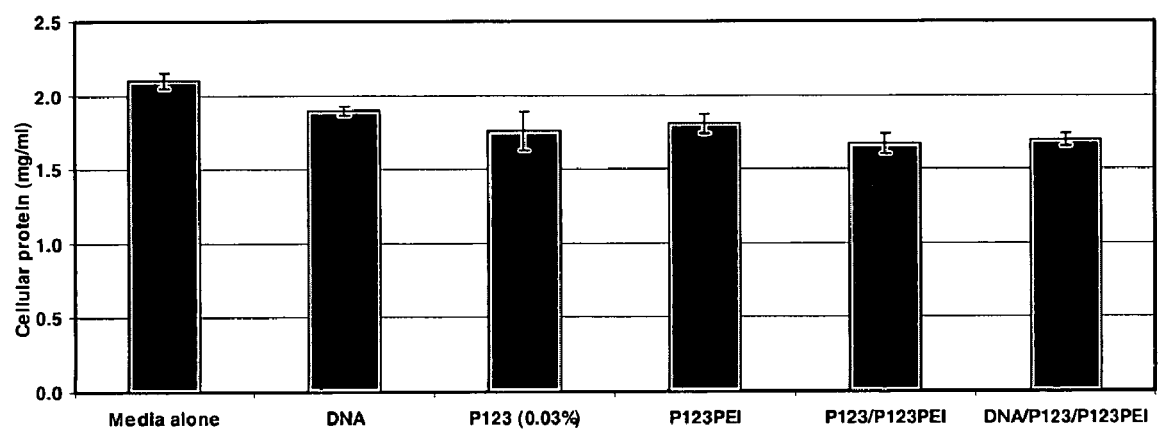

FIG. 6A is a graph of the luciferase present in Luc-NIH3T3 cells treated with media alone or media containing DNA, 0.03% P123, 0.8 µM PEI-P123, P123/P123-PEI, or DNA and P123/P123-PEI. FIG. 6B is a graph of the total cellular protein of the above-identified cells. The data is reported as mean ± SD (N=3).

DETAILED DESCRIPTION OF THE INVENTION

In accordance with the present invention, compositions and methods for the production of a protein are provided. The method of the instant invention can be employed to increase the production of protein from a cell in any setting such as, without limitation, cells in tissue culture on a laboratory scale and cells employed in large-scale production of recombinant proteins, particularly proteins having therapeutic value. Notably, the increase in protein production is observed 1) without the addition of metal ions such as copper ions and 2) in the presence of media containing protein derived from a human or animal.

In a particular embodiment of the invention, increased protein production is obtained by incubating a cell comprising a nucleic acid encoding a recombinant protein in the presence of an amphiphilic polymer. The cell of the instant invention can be selected from the group consisting of bacteria cells (e.g., *E. coli*), insect cells (e.g., SF9, Sf21, High five), yeast cells (e.g., *S. cerevisiae, P. pastoris*), and mammalian cells (including cells typically employed for mass production of recombinant proteins such as, without limitation, baby hamster kidney cells (BHK), Chinese hamster ovary cells (CHO), human embryonic kidney cells (HEK), C127 cells, Cos cells). Preferably, the cell is a mammalian cell. The cells may be a cell line or may be a part of a tissue (e.g., a biopsy).

The cells of the instant method are preferably stably transformed with a heterologous DNA. In a particular embodiment, the cells are stably transfected.

According to one aspect of the invention, the nucleic acid encoding the recombinant protein is under the control of a promoter. In a particular embodiment, the promoter is heterologous to the cell from which the recombinant protein is to be expressed. In a particular embodiment, the promoter is selected from the group consisting of the cytomegalovirus immediate early (CMV-IE) promoter, the simian virus 40 (SV40) early promoter, herpes simplex virus (HSV) thymidine kinase (tk) promoter, the RSV (Rous sarcoma virus) promoter, and the Adenovirus major late promoter. In a preferred embodiment, the promoter is the CMV-IE promoter.

Additionally, the genes encoding the recombinant protein of the instant invention may be under the control of a transcription element present in the cell such as, without limitation, elements containing the binding sites for the transcription factors NF-κB and p53.

Notably, the promoters of the invention may be the natural promoters or may be allelic variants or derivatives thereof. For example, the CMV promoter of the gWIZ plasmid (Gene Therapy Systems, San Diego, Calif.) contains a modified CMV promoter which allows for greater expression levels. Additionally, the promoters may be associated with their natural enhancer elements or with heterologous enhancer elements. The enhancer elements may be wild-type, allelic variants, or derivatives thereof.

The cells to be treated by the methods of the instant invention can be in a variety of settings. For example, the cells can be in culture such as in a small scale tissue culture or in culture conditions conducive to the large scale production of recombinant proteins. Alternatively, in another embodiment, the cells are treated ex vivo and then introduced into a patient.

The present invention also encompasses kits for use in effecting enhanced expression of a protein or RNA of interest. Such kits comprise an amphiphilic block polymer, reagents to transform a cell, and selection media to isolate stably transformed cells. The kits may further comprise frozen stocks of host cells and instruction manuals. As used herein, an "instructional material" includes a publication, a recording, a diagram, or any other medium of expression which can be used to communicate the usefulness of the composition of the invention for performing a method of the invention. The instructional material of the kit of the invention can, for example, be affixed to a container which contains a kit of the invention to be shipped together with a container which contains the kit. Alternatively, the instructional material can be shipped separately from the container with the intention that the instructional material and kit be used cooperatively by the recipient.

I. Definitions

The following definitions are provided to facilitate an understanding of the present invention:

As used herein, the term "polymer" denotes molecules formed from the chemical union of two or more repeating units. The term "block copolymer" most simply refers to conjugates of at least two different polymer segments, wherein the polymer segments comprise two or more adjacent units of the same kind.

As used herein, the term "lipophilic" refers to the ability to dissolve in lipids.

As used herein, the term "hydrophilic" means the ability to dissolve in water.

As used herein, the term "amphiphilic" means the ability to dissolve in both water and lipids. Typically, an amphiphilic compound or substance comprises a hydrophilic portion and a lipophilic portion.

The term "polycation" means a polymeric molecule having a plurality of positive charges distributed thereon. Examples of polycations include, without limitation, polyamines (e.g., spermine, polyspermine, polyethyleneimine, polypropyleneimine, polybutileneimine, polypentyleneimine, polyhexyleneimine and copolymers thereof); copolymers of tertiary amines and secondary amines; partially or completely quaternized amines; polyvinyl pyridine; quaternary ammonium salts of a polycation; cationic dendrimers such as polyamidoamines and polypropyleneimines; aliphatic, heterocyclic or aromatic ionenes; polyamides; protamine sulfate; polybrene; polylysine; polyarginine; and chitosan. Polycations may also be a plurality of cationic repeating units of the formula —N—R$^o$, wherein R$^o$ is a straight chain aliphatic group of 2 to 6 carbon atoms, which may be substituted. Each —N—R$^o$— repeating unit in a polycation can be the same or different from another —N—R$^o$— repeating unit in the polycation. The polycations may also be branched such as the products of polycondensation or the condensation reactions between polyamines containing at least 2 nitrogen atoms and alkyl halides containing at least 2 halide atoms (including bromide or chloride). An example of a branched polycation is polyethyleneimine represented by the formula: —(NHCH$_2$CH$_2$)$_x$[N(CH$_2$CH$_2$NH$_2$)CH$_2$CH$_2$]$_y$—, obtainable from, for example, Sigma (St. Louis, Mo.) and BASF.

The term "recombinant protein" refers to a protein prepared by recombinant DNA techniques, wherein generally, DNA encoding the protein is inserted into a suitable expression vector which is in turn used to transform a host cell to produce the protein. The protein may or may not be heterologous, i.e. did not exist as part of the cell prior to the transformation.

The term "isolated" as used in connection with an "isolated protein" refers to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like). "Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. For example, a vertebrate promoter may be used for the expression of jellyfish GFP in vertebrates. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art.

The term "enhancers" or "enhancer" as used herein can refer to a DNA sequence that is located adjacent to the DNA sequence that encodes a recombinant product. Enhancer elements are typically located upstream of a promoter element or can be located downstream of or within a coding DNA sequence (e.g., a DNA sequence transcribed or translated into a recombinant product or products). Hence, an enhancer element can be located 100 base pairs, 200 base pairs, or 300 or more base pairs upstream or downstream of a DNA sequence that encodes recombinant product. Enhancer elements can increase an amount of recombinant product expressed from a DNA sequence above the level of expression afforded by a promoter element. Multiple enhancer elements are readily available to persons of ordinary skill in the art.

"Natural allelic variants", "mutants" and "derivatives" of particular sequences of nucleic acids refer to nucleic acid sequences that are closely related to a particular sequence but which may possess, either naturally or by design, changes in sequence or structure. By closely related, it is meant that at least about 75%, but often, more than 90%, of the nucleotides of the sequence match over the defined length of the nucleic acid sequence referred to using a specific SEQ ID NO. Changes or differences in nucleotide sequence between closely related nucleic acid sequences may represent nucleotide changes in the sequence that arise during the course of normal replication or duplication in nature of the particular nucleic acid sequence. Other changes may be specifically designed and introduced into the sequence for specific purposes, such as to change an amino acid codon or sequence in a regulatory region of the nucleic acid. Such specific changes may be made in vitro using a variety of mutagenesis techniques or produced in a host organism placed under particular selection conditions that induce or select for the changes. Such sequence variants generated specifically may be referred to as "mutants" or "derivatives" of the original sequence.

A "replicon" is any genetic element, for example, a plasmid, cosmid, bacmid, phage or virus, which is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression vector" refers to a vector which facilitates the expression of a polypeptide coding sequence in a host cell or organism.

The term "gene" refers to a nucleic acid comprising an open reading frame encoding a polypeptide, including both exon and (optionally) intron sequences. The nucleic acid may also optionally include non-coding sequences such as promoter or enhancer sequences. The term "intron" refers to a DNA sequence present in a given gene that is not translated into protein and is generally found between exons.

The terms "stably transformed", "stably transfected," "stably incorporated" and variations thereof refer to the incorporation of heterologous DNA into a cell, preferably into the chromosomes of the cell, where it is expressed for at least the remainder of the life time of the cell. Preferably, the heterologous DNA is expressed by future generations of cells derived from the originally transformed cell. Stable transformation of a cell may be distinguished from transient expression of heterologous DNA by a cell by, for example, the length of time the recipient cell expresses the heterologous DNA. With transient expression, the cell generally expresses the heterologous protein for a few days or weeks until the vector containing the heterologous DNA is lost from the cell. With stable transformation, the heterologous DNA is expressed for longer periods of time and is passed to later generations of the cells. The heterologous DNA is typically a part of an expression vector. The heterologous DNA may be introduced into the cell by any method such as, without limitation, microinjection, transfection, lipofection, transduction, transformation, and electroporation.

The term "reagents to transform a cell" refers to any reagents that can be employed to assist the transformation of a cell by any method such as by microinjection, transfection, lipofection, transduction, transformation, and electroporation (see generally, Ausubel et al., eds. Current Protocols in Molecular Biology, John Wiley and Sons, Inc., (1998)). Specific examples of such reagents include, without limitation, vectors, buffers, and solutions comprising $CaPO_4$, lipofectamine™, and/or polyethyleneglycol (PEG).

The term "selection agent" refers to a substance, such as an antibiotic, that interferes with the growth or survival of a host cell that has not been successfully transformed with a gene that confers resistance to the selection agent.

The term "gene therapy" refers to the transfer of genetic material (e.g., DNA or RNA) of interest into a host (e.g., a human or an animal) to treat or prevent a genetic or acquired disease or condition. The genetic material of interest encodes a product, particularly a protein, of therapeutic value whose production in vivo is desired.

The term "ex vivo gene therapy" refers to the in vitro transfer of genetic material (e.g., DNA or RNA) of interest into a cell and then introducing the transformed cells into a host (see, for example, U.S. Pat. No. 5,399,346). The cells may be isolated from the host prior to transformation or may be obtained from a different source such as a different animal or human donor.

The phrase small, interfering RNA (siRNA) refers to a double stranded RNA molecule (RNA is usually single stranded) which inhibits expression of its cognate mRNA (see, e.g. Ausubel et al., eds. Current Protocols in Molecular Biology, John Wiley and Sons, Inc., (1998)). A short hairpin RNA molecule (shRNA) typically consists of short inverted repeats separated by a small loop sequence. Generally, one of the inverted repeats is complimentary to the gene target. Additionally, the shRNA is typically processed into an siRNA within the cell by endonucleases. siRNAs and shRNAs specific for a protein of interest can downregulate its expression. Such RNAs are typically expressed from RNA polymerase III promoters such as, without limitation, the U6 and H1 promoters (see, e.g., Myslinski et al. (2001) Nucl. Acids Res., 29:2502-09).

II. Amphiphilic Polymers

Amphiphilic polymers according to the instant invention are preferably amphiphilic block copolymers. Amphiphilic block copolymers are exemplified by the block copolymers having the formulas:

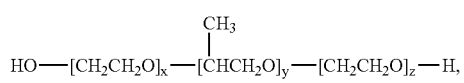

(I)

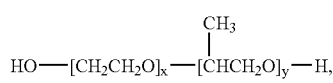

(II)

(III)

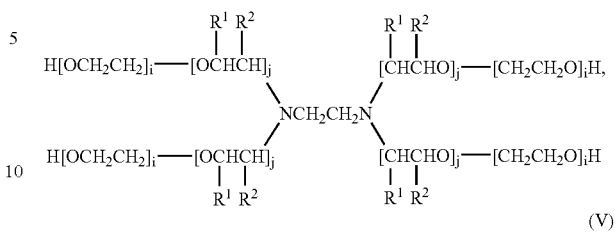

(IV)

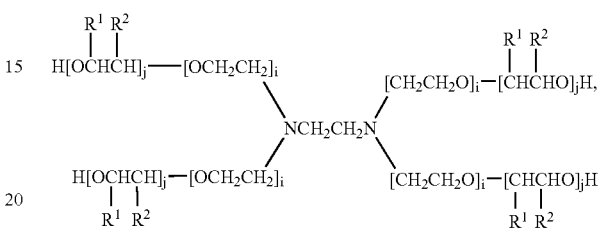

(V)

in which x, y, z, i, and j have values from about 2 to about 800, preferably from about 5 to about 200, more preferably from about 5 to about 80, and wherein for each $R^1$, $R^2$ pair, as shown in formula (IV) and (V), one is hydrogen and the other is a methyl group. Formulas (I) through (III) are oversimplified in that, in practice, the orientation of the isopropylene radicals within the B block will be random. This random orientation is indicated in formulas (IV) and (V), which are more complete. Such poly(oxyethylene)-poly(oxypropylene) compounds have been described by Santon (Am. Perfumer Cosmet. (1958) 72(4):54-58); Schmolka (Loc. cit. (1967) 82(7):25-30), Schick, ed. (Non-ionic Suifactants, Dekker, N.Y., 1967 pp. 300-371). A number of such compounds are commercially available under such generic trade names as "lipoloxamers", "Pluronics®," "poloxamers," and "synperonics." Pluronic® copolymers within the B-A-B formula, as opposed to the A-B-A formula typical of Pluronics®, are often referred to as "reversed" Pluronics®, "Pluronic® R" or "meroxapol." Generally, block copolymers can be described in terms of having hydrophilic "A" and hydrophobic "B" block segments. Thus, for example, a copolymer of the formula A-B-A is a triblock copolymer consisting of a hydrophilic block connected to a hydrophobic block connected to another hydrophilic block.

The "polyoxamine" polymer of formula (IV) is available from BASF under the tradename Tetronic®. The order of the polyoxyethylene and polyoxypropylene blocks represented in formula (IV) can be reversed, creating Tetronic R®, also available from BASF (see, Schmolka, J. Am. Oil. Soc. (1979) 59:110).

Polyoxypropylene-polyoxyethylene block copolymers can also be designed with hydrophilic blocks comprising a random mix of ethylene oxide and propylene oxide repeating units. To maintain the hydrophilic character of the block, ethylene oxide can predominate. Similarly, the hydrophobic block can be a mixture of ethylene oxide and propylene oxide repeating units. Such block copolymers are available from BASF under the tradename Pluradot™.

The hydrophobic/hydrophilic properties of a given block copolymer depends upon the ratio of the number of oxypropylene groups to the number of oxyethylene groups. For a composition containing a single block copolymer of poly (oxyethylene)-poly(oxypropylene), for example, this relationship, taking into account the molecular masses of the central hydrophobic block and the terminal hydrophilic blocks, can be expressed as follows:

$$n = (H/L)(1.32)$$

in which H is the number of oxypropylene units and L is the number of oxyethylene units. In the general case of a block copolymer containing hydrophobic B-type segments and hydrophilic A-type segments, the hydrophobic-hydrophilic properties and micelle-forming properties are related to the value n as defined as:

$$n = (|B|/|A|) \times (b/a)$$

where |B| and |A| are the number of repeating units in the hydrophobic and hydrophilic blocks of the copolymer, respectively, and b and a are the molecular weights for the respective repeating units.

Selecting a block copolymer with the appropriate n value depends upon the hydrophobic/hydrophilic properties of the specific agent, or the composite hydrophilic/hydrophobic properties of a mixture of agents to be formulated. One aspect of the present invention involves utilizing a mixture of different block-copolymers of poly(oxyethylene)-poly(oxypropylene) to achieve a more specific hydrophobic-hydrophilic balance. For example, a first block copolymer may have an n of 1.0 whereas a second may have a value of 1.5. If material having an n of 1.3 is desired, a mixture of one weight portion of the first block copolymer and 1.5 weight portion of the second block-copolymer can be employed.

Thus, a more generalized relationship for such mixtures can be expressed as follows:

$$N = (1.32)[(H_1 m_1)/((L_1)(m_1+m_2)) + (H_2 m_2)/((L_2)(m_1+m_2))]$$

in which $H_1$ and $H_2$ are the number of oxypropylene units in the first and second block copolymers, respectively; $L_1$ is the number of oxyethylene units in the first block copolymer; $L_2$ is the number of oxyethylene units in the second block copolymer; $m_1$ is the weight proportion in the first block-copolymer; and $m_2$ is the weight proportion in the second block copolymer.

An even more general case of a mixture of K block copolymers containing hydrophobic B-type block copolymers and hydrophilic A-type block copolymers, the N value can be expressed as follows:

$$N = (b/a) \sum_{i=1}^{k} [(|B|_i/|A|_i), (m_i/M)]$$

where $|A|_i$ and $|B|_i$ are the numbers of repeating units in the hydrophilic (A-type) and hydrophobic (B-type) blocks of the i-th block copolymer, m is the weight proportion of this block copolymers, M is the sum of weight proportions of all block copolymers in the mixture $$M = \sum_{i=1}^{k} m_i$$

and a and b are the molecular weights for the repeating units of the hydrophilic and hydrophobic blocks of these block copolymers, respectively.

If only one block copolymer of poly(oxyethylene)-poly (oxypropylene) is utilized, N will equal n. An analogous relationship will apply to compositions employing more than two block copolymers of poly(oxyethylene)-poly(oxypropylene) (EO-PO). Where mixtures of block copolymers are used, a value N will be used, which value will be the weighted average of n for each contributing copolymer, with the averaging based on the weight portions of the component copolymers. The value N can be used to estimate the micelle-forming properties of a mixture of copolymers. The use of the mixtures of block copolymers enhances solubility and prevents aggregation of more hydrophobic block copolymers in the presence of the serum proteins.

A number of Pluronic® copolymers are designed to meet the following formula:

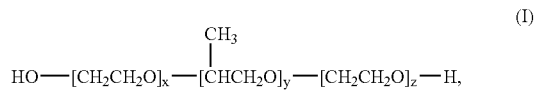

The ordinarily skilled artisan will recognize that the values of x, y, and z will usually represent a statistical average and that the values of x and z are often, though not necessarily, the same. The characteristics of a number of Pluronic® copolymers corresponding to formula (I) are as follows:

TABLE 1

| Copolymer | Hydrophobe Weight | CMC (% w/v) | Hydrophobe percentage |
|---|---|---|---|
| Pluronic ® L61 | 1750 | 0.0003 | 90 |
| Pluronic ® L64 | 1750 | 0.002 | 60 |
| Pluronic ® F68 | 1750 | 4-5 | 20 |
| Pluronic ® P85 | 2250 | 0.005-0.007 | 50 |
| Pluronic ® F127 | 4000 | 0.003-0.005 | 30 |
| Pluronic ® F108 | 3250 | 0.0035-0.007 | 20 |

These critical micelle concentrations (CMC) values were determined by the surface tension method described in Kabanov et al. (Macromolecules (1995) 28: 2303-2314).

These block copolymers can be prepared by the methods set out, for example, in U.S. Pat. No. 2,674,619 and are commercially available from BASF under the trademark Pluronic®. Pluronic® block copolymers are designated by a letter prefix followed by a two or a three digit number. The letter prefixes (L, P, or F) refer to the physical form of each polymer, (liquid, paste, or flakeable solid). The numeric code defines the structural parameters of the block copolymer. The last digit of this code approximates the weight content of EO block in tens of weight percent (for example, 80% weight if the digit is 8, or 10% weight if the digit is 1). The remaining first one or two digits encode the molecular mass of the central PO block. To decipher the code, one should multiply the corresponding number by 300 to obtain the approximate molecular mass in daltons (Da). Therefore Pluronic nomenclature provides a convenient approach to estimate the characteristics of the block copolymer in the absence of reference literature. For example, the code 'F127' defines the block copolymer, which is a solid, has a PO block of 3600 Da (12×300) and 70% weight of EO. The precise molecular characteristics of each Pluronic® block copolymer can be obtained from the manufacturer. Additional specific poly (oxyethylene)-poly(oxypropylene) block copolymers which can be used in practicing this invention include the Pluronic® and Pluronic®-R block copolymers of Table 2.

TABLE 2

| Pluronic® | Hydrophobe Weight | Hydrophobe % | Pluronic-R® | Hydrophobe Weight | Hydrophobe % |
|---|---|---|---|---|---|
| L31 | 950 | 90 | 10R5 | 1000 | 50 |
| L35 | 950 | 50 | 10R8 | 1000 | 20 |
| F38 | 900 | 20 | 12R3 | 1200 | 70 |
| L42 | 1200 | 80 | 17R1 | 1700 | 90 |
| L43 | 1200 | 70 | 17R2 | 1700 | 80 |
| L44 | 1200 | 60 | 17R4 | 1700 | 60 |
| L61 | 1750 | 90 | 17R8 | 1700 | 20 |
| L62 | 1750 | 80 | 22R4 | 2200 | 60 |
| L63 | 1750 | 70 | 25R1 | 2500 | 90 |
| L64 | 1750 | 60 | 25R2 | 2500 | 80 |
| P65 | 1750 | 50 | 25R4 | 2500 | 60 |
| F68 | 1750 | 20 | 25R5 | 2500 | 50 |
| L72 | 2050 | 80 | 25R8 | 2500 | 50 |
| P75 | 2050 | 50 | 31R1 | 3100 | 90 |
| F77 | 2050 | 30 | 31R2 | 3100 | 80 |
| L81 | 2250 | 90 | 31R4 | 3100 | 60 |
| P84 | 2250 | 60 | | | |
| P85 | 2250 | 50 | | | |
| F87 | 2250 | 30 | | | |
| F88 | 2250 | 20 | | | |
| L92 | 2750 | 80 | | | |
| F98 | 2750 | 20 | | | |
| L101 | 3250 | 90 | | | |
| P103 | 3250 | 70 | | | |
| P104 | 3250 | 60 | | | |
| P105 | 3250 | 50 | | | |
| F108 | 3250 | 20 | | | |
| L121 | 4000 | 90 | | | |
| L122 | 4000 | 80 | | | |
| L123 | 4000 | 70 | | | |
| F127 | 4000 | 30 | | | |

Other specific poly(oxyethylene)-poly(oxypropylene) block copolymers which can be included in compositions described herein are the Tetronic® and Tetronic® R nonionic surfactants of formula (IV) and (V), above, which are tetrafunctional block copolymers derived from the addition of ethylene oxide and propylene oxide to ethylenediamine. Tetronic® and Tetronic® R copolymers include, without limitation, those set forth in Table 3.

TABLE 3

| Tetronic® | Form | HLB | Average MW |
|---|---|---|---|
| 304 | Liquid | 16 | 1650 |
| 701 | Liquid | 3 | 3600 |
| 704 | Liquid | 15 | 5500 |
| 901 | Liquid | 3 | 4700 |
| 904 | Liquid | 15 | 6700 |
| 908 | Solid | 31 | 25000 |
| 1107 | Solid | 24 | 15000 |
| 1301 | Liquid | 2 | 6800 |
| 1307 | Solid | 24 | 18000 |
| 90R4 | Liquid | 7 | 7240 |
| 150R1 | Liquid | 1 | 8000 |

In selecting copolymers for use in the instant invention, poly(oxyethylene)-poly(oxypropylene) block units making up the first segment need not consist solely of ethylene oxide. Nor is it necessary that all of the B-type segment consist solely of propylene oxide units. Instead, in the simplest cases, for example, at least one of the monomers in segment A may be substituted with a side chain group.

In addition, the present invention can also be practiced using diamine-linked polyoxyethylene-polyoxypropylene polymers of formula:

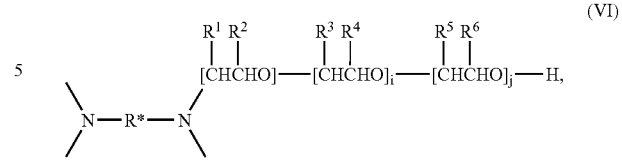

(VI)

wherein the same number and sequence of polyether moieties extend symetrically from the second nitrogen, R* is an alkylene of about 2 to about 6 carbons, a cycloalkylene of about 5 to about 8 carbons or phenylene, $R^1$ and $R^2$, either (a) both represent hydrogen or (b) one represents hydrogen and the other represents methyl, for $R^3$ and $R^4$ either (a) both are hydrogen or (b) one is hydrogen and the other is methyl; if both of $R^3$ and $R^4$ represent hydrogen, then one of $R^5$ and $R^6$ represents hydrogen and the other is methyl; and both of $R^5$ and $R^6$ represent hydrogen when $R^3$ and $R^4$ each represent hydrogen. The polyoxyethylene-polyoxypropylene polymers may be, for example, Pluronic® or Pluronic®-R.

Over 30 Pluronic® copolymers with different lengths of hydrophilic ethylene oxide ($N_{EO}$) and hydrophobic propylene oxide ($N_{PO}$) blocks are available from BASF Corp. (see, for example, Table 2). These molecules are characterized by different hydrophilic-lipophilic balance (HLB) and CMC (Kozlov et al. (2000) Macromolecules, 33:3305-3313; see, for example, Table 3). The HLB value reflects the balance of the size and strength of the hydrophilic groups and lipophilic groups of the polymer (see, for example, Attwood and Florence (1983) "Surfactant Systems: Their Chemistry, Pharmacy and Biology," Chapman and Hall, New York) and can be determined experimentally by, for example, the phenol titration method of Marszall (see, for example, "Parfumerie, Kosmetik", Vol. 60, 1979, pp. 444-448; Rompp, Chemistry Lexicon, 8th Edition 1983, p. 1750; U.S. Pat. No. 4,795,643). Notably, as hydrophobicity increases, HLB decreases.

TABLE 4

| Pluronic® | MW [a] | $N_{PO}$ [b] | $N_{EO}$ [b] | HLB [a] | CMC, µM [c] |
|---|---|---|---|---|---|
| L31 | 1100 | 17.1 | 2.5 | 5 | 1180 |
| L35 | 1900 | 16.4 | 21.6 | 19 | 5260 |
| F38 | 4700 | | | 31 | |
| L42 | 1630 | | | 8 | |
| L43 | 1850 | 22.3 | 12.6 | 12 | 2160 |
| L44 | 2200 | 22.8 | 20.0 | 16 | 3590 |
| L61 | 2000 | 31 | 4.5 | 3 | 110 |
| L62 | 2500 | 34.5 | 11.4 | 7 | 400 |
| L63 | 2650 | | | 11 | |
| L64 | 2900 | 30 | 26.4 | 15 | 480 |
| P65 | 3400 | | | 17 | |
| F68 | 8400 | 29 | 152.7 | 29 | 480 |
| L72 | 2750 | | | 7 | |
| P75 | 4150 | | | 17 | |
| F77 | 6600 | | | 25 | |
| L81 | 2750 | 42.7 | 6.2 | 2 | 23 |
| P84 | 4200 | 43.4 | 38.2 | 14 | 71 |
| P85 | 4600 | 39.7 | 52.3 | 16 | 65 |
| F87 | 7700 | 39.8 | 122.5 | 24 | 91 |
| F88 | 11400 | 39.3 | 207.8 | 28 | 250 |
| L92 | 3650 | 50.3 | 16.6 | 6 | 88 |
| F98 | 13000 | 44.8 | 236.4 | 28 | 77 |
| L101 | 3800 | 58.9 | 8.6 | 1 | 2.1 |
| P103 | 4950 | 59.7 | 33.8 | 9 | 6.1 |
| P104 | 5900 | 61.0 | 53.6 | 13 | 3.4 |
| P105 | 6500 | 56.0 | 73.9 | 15 | 6.2 |
| F108 | 14600 | 50.3 | 265.4 | 27 | 22 |
| L121 | 4400 | 68.3 | 10.0 | 1 | 1 |
| L122 | 5000 | | | 4 | |

TABLE 4-continued

| Pluronic® | MW [a] | $N_{PO}$ [b] | $N_{EO}$ [b] | HLB [a] | CMC, µM [c] |
|---|---|---|---|---|---|
| P123 | 5750 | 69.4 | 39.2 | 8 | 44 |
| F127 | 12600 | 65.2 | 200.4 | 22 | 2.8 |
| 10R5 | 1950 | | | 15 | |
| 10R8 | 4550 | | | 19 | |
| 12R3 | 1800 | | | 7 | |
| 17R1 | 1900 | | | 3 | |
| 17R2 | 2150 | | | 6 | |
| 17R4 | 2650 | | | 12 | |
| 17R8 | 7000 | | | 16 | |
| 22R4 | 3350 | | | 10 | |
| 25R1 | 2700 | | | 2 | |
| 25R2 | 3100 | | | 4 | |
| 25R4 | 3600 | | | 8 | |
| 25R5 | 4250 | | | 10 | |
| 25R8 | 8550 | | | 13 | |
| 31R1 | 3250 | | | 1 | |
| 31R2 | 3300 | | | 2 | |
| 31R4 | 4150 | | | 7 | |

[a] The average molecular weights and HLB provided by the manufacturer (BASF Co.);
[b] The average numbers of EO and PO units were calculated using the average molecular weights of the blocks;
[c] Critical micelle concentration (CMC) values at 37° C. were determined using pyrene probe (Kozlov et al. (2000) Macromolecules, 33: 3305-3313).

Preferably, the amphiphilic polymer is a copolymer of poly(oxyethylene) and poly(oxypropylene), more preferably the amphiphilic polymer is a Pluronic® copolymer. Preferably, the amphiphilic copolymer possesses an HLB of less than or equal to 20, more preferably an HLB of less than or equal to 16, and most preferably an HLB of between 8 and 16. Such Pluronics® include, for example, Pluronic® P123, Pluronic® P103, Pluronic® P85, Pluronic® L64, and others.

In a particular embodiment of the invention, the amphiphilic block polymers are present in the media at a concentration ranging from about 0.0001% to about 5%. In a particular embodiment, the concentration of the Pluronic® copolymers ranges from about 0.1% to about 2%.

III. Proteins

The expression product of the invention may be an protein, a peptide, or polypeptide. The compositions and methods of the instant invention can be employed to increase the expression of any protein.

The increased production of protein by the methods of the instant invention will prove useful in the field of recombinant protein expression, particularly in the production of large quantities of therapeutic proteins, and especially from mammalian cells. Indeed, for recombinantly produced proteins that are intended for commercial use, in particular, it is desirable to obtain a high level of expression of the desired protein from each host cell. Increasing the amount of desired protein produced per cell can reduce costs of production due to the decreased volume of cells that must be grown to obtain a given amount of product, and also can facilitate purification because the desired product makes up a larger percentage of the total protein produced by the host cells.

Some of the factors that may be considered when selecting a protein expression system are (1) the success of expression of the protein in various systems and (2) the requirement for glycosylation and other post-translational modifications. Each of these factors can be successfully accounted for by the system described herein which provides for increased production of active protein from mammalian cells, wherein post-translational modifications may occur.

Exemplary proteins for use in the instant invention include, without limitation, cytokines, enzymes, clotting factors (e.g., Factor VIII, Factor IX, angiostatin, tissue plasminogen activator (tPA)), vaccines, antibodies (e.g., monoclonal antibodies), growth factors and hormones (e.g., erythropoietin), insulin, hemoglobin, alpha-1-antitrypsin (AAT), lactoferrin, cystic fibrosis transmembrane conductase (CFTR), human protein C, anti-viral agents, and interleukins (e.g., interleukin-2).

The following examples provide illustrative methods of practicing the instant invention, and are not intended to limit the scope of the invention in any way. While certain of the following examples specifically recite a specific type of Pluronic® block copolymer (e.g., Pluronic® P85), the use of any amphiphilic polymer is within the scope of the instant invention.

EXAMPLE 1

Increased Production of Luciferase

Luc-NIH3T3 cells were generated by transfecting NIH3T3 cells with a 5:1 mixture of plasmids gWIZ™-Luc and phCMV1 (both from Gene Therapy Systems, San Diego, Calif.) using ExGen500 (Fermentas Inc., Hanover, Md.) as described in Gebhart and Kabanov (J. Contr. Release (2001) 73:1767-1775). Plasmid gWIZ™-Luc contains the gene encoding for luciferase under the control of a cytomegalovirus (CMV) immediate early (IE) promoter/enhancer. Plasmid phCMV1 contains the G418 resistance gene. The luciferase expressing clones (Luc-NIH3T3) were selected using standard G418 selection procedures (Ausubel et al. (1992) Short Protocols in Molecular Biology, John Wiley and Sons) and maintained in Dulbecco's Modified Eagle's Medium (DMEM) containing 400 µg/ml G418.

Luc-NIH3T3 cells were seeded in 24-well plates at $5 \times 10^4$ cells per well. The cells were grown to about 70% confluency and then exposed to various concentrations of Pluronic® P85 for 3 hours. The cells were then washed and incubated for 24 hours in 0.5 ml of DMEM with 10% fetal bovine serum (FBS). The cells were then lysed in 100 µl of 1× CCLR (cell culture lysis reagent; Promega, Madison, Wis.) and the luciferase activity was measured using the Luciferase Assay System (Promega) as described in Gebhart and Kabanov (J. Contr. Release (2001) 73:1767-1775). Total cellular protein in lysates was measured with the BCA protein assay (Pierce, Rockford, Ill.). The protein levels of the various lysates were within 20%.

Figure 1:
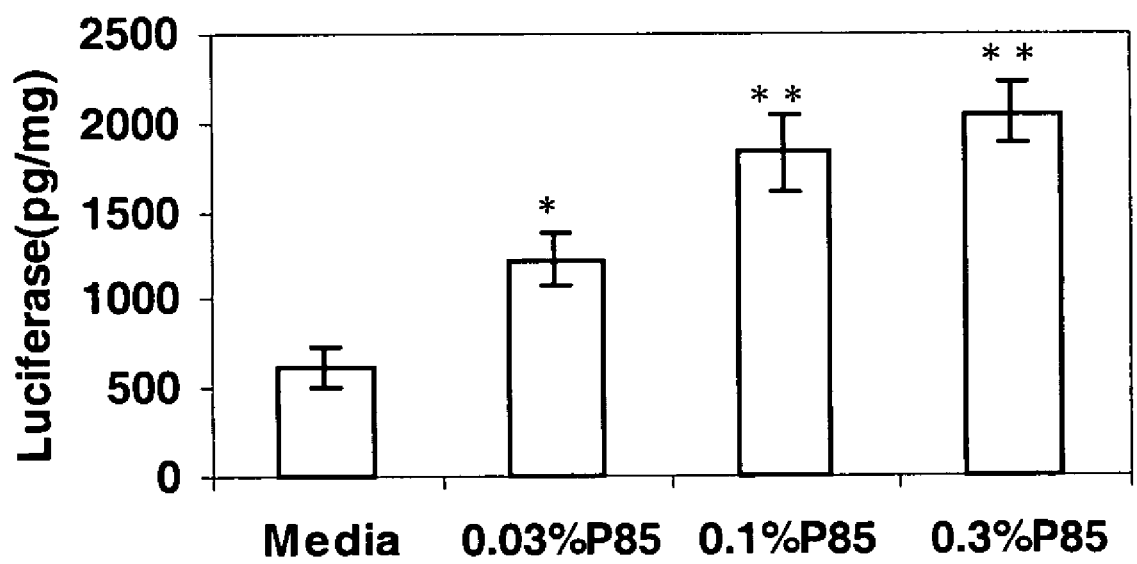

As seen in FIG. 1, the presence of Pluronic® P85 resulted in a significant increase in the yield of luciferase from the Luc-NIH3T3 cells. Indeed, treatment with increasing amounts of Pluronic® P85 led to increased luciferase production. Notably, Pluronic® P85 had no effect on the activity of luciferase as the luminescence of cellular lysates increased at the same rate as the protein levels of luciferase.

Figure 2:
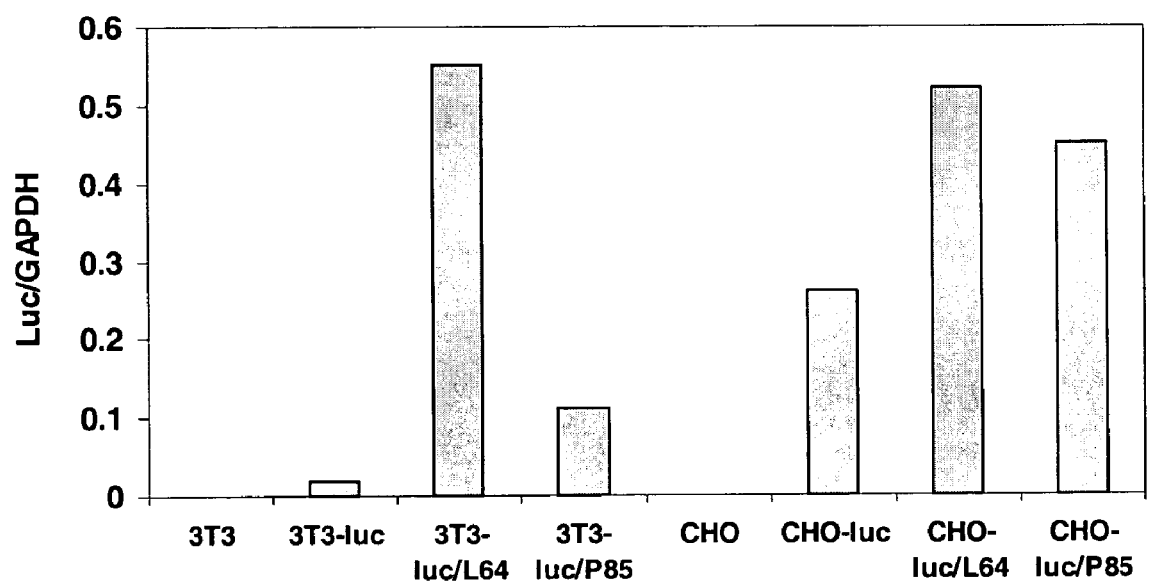
FIG. 2 is a graph of the ratio of luciferase mRNA to GAPDH mRNA present in cells treated with media alone or media containing Pluronic® L64 or P85. The cells assayed are NIH3T3, Luc-NIH3T3, CHO, and CHO-luc cells.

The effect of the Pluronic® copolymers was also tested on different cell types to demonstrate that the effect was not limited to NIH3T3 cells. Specifically, CHO (Chinese hamster ovary) cells stably transfected with the luciferase gene (CHO-Luc) were generated by the same methods as that used to generate the Luc-NIH3T3 cells. The cells were incubated for 3 hours with either Pluronic® L64 or P85. The mRNA levels of luciferase and the housekeeping gene D-glyceraldehyde-3-phosphate dehydrogenase (GADPH) were then obtained by a standard RT-PCR assay. As seen in FIG. 2, the presence of either Pluronic® L64 or P85 led to a significant increase in the production of luciferase compared to cells not treated with a Pluronic®, regardless of the cell type. Furthermore, the increase in the ratio of luciferase to GAPDH production suggests that the effect of the Pluronic® is specific to heterologous or foreign promoters.

EXAMPLE 2

Increased Production of Green Fluorescent Protein

GFP-C166 cells were generated by transfecting C166 cells with plasmid pEGFPN1 (Clontech, Palo Alto, Calif.) using ExGen500 (Fermentas Inc., Hanover, Md.) as described in Gebhart and Kabanov (J. Contr. Release (2001) 73:1767-1775). Plasmid pEGFPN1 contains the gene encoding for green fluorescent protein (GFP) under the control of a cytomegalovirus (CMV) immediate early (IE) promoter/enhancer and contains the G418 resistance gene. The GFP expressing clones (GFP-C166) were selected using standard procedures (Ausubel et al. (1992) Short Protocols in Molecular Biology, John Wiley and Sons) and maintained in Dulbecco's Modified Eagle's Medium (DMEM) containing 400 µg/ml G418.

GFP-C166 cells were seeded in 12 well plates at $8 \times 10^4$ cells per well. The cells were allowed to grow to about 70% confluency and were then exposed to Pluronic® P85 for 3, 6, or 9 hours. The cells were then incubated for 24 hours in 1 ml of DMEM with 10% FBS. Following the 24 hour incubation, the cells were detached by trypsin, washed, and resuspended in phosphate-buffered saline (PBS) with 1% FBS. 10,000 cells were then analyzed for GFP fluorescence using a FACStar Plus™ flow cytometer (Becton Dickinson, San Jose, Calif.) operating under Lysis II (excitation—488 nm; emission filter—530±30 nm).

Figure 3:
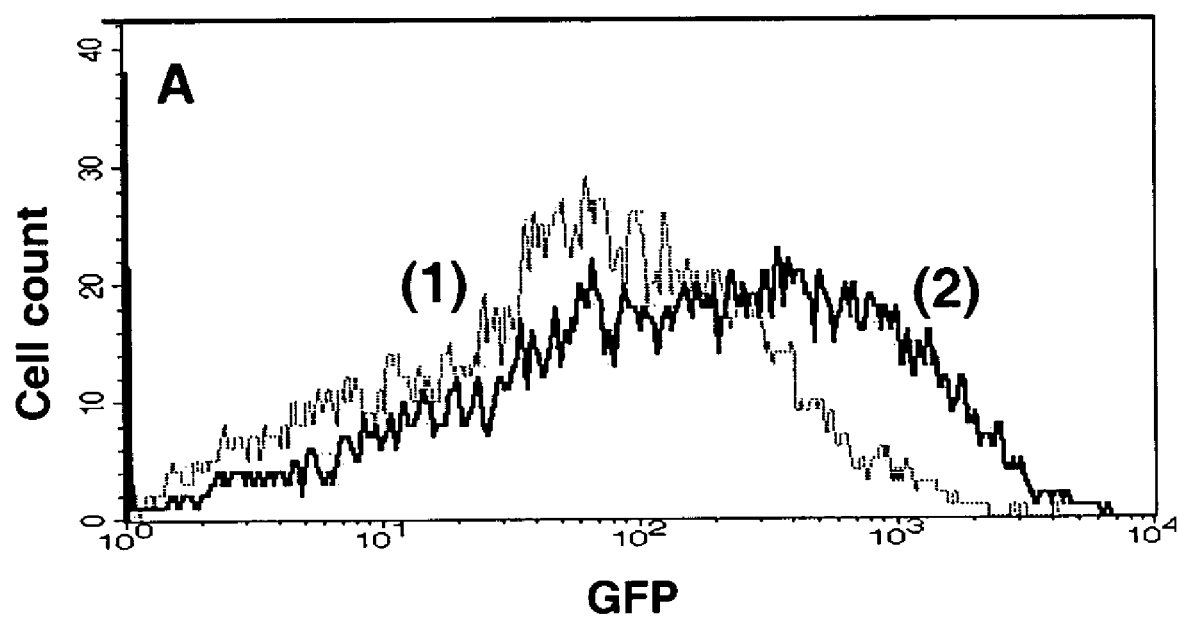
FIG. 3 is a graph of the intensity of fluorescence of GFP-C166 cells treated with media as a control (1) or treated with 0.1% Pluronic® P85 for 9 hours (2).

As seen in FIG. 3, GFP-C166 cells treated for 9 hours with Pluronic® P85 expressed significantly more GFP than cells that were untreated. Notably, a similar timecourse was seen with L64 on Luc-NIH3T3 cells. Furthermore, longer treatments yielded greater GFP production (FIG. 4). Notably, similar effects were noted with luciferase production wherein luciferase production was greatly increased after 9 hours of exposure to L64.

Notably, Pluronic® P123 was also assayed for the ability to increase the production of GFP from GFP-C166 cells. As with Pluronic® P85, treatment with Pluronic® P123 resulted in the increase production of P123, but required slightly higher concentrations to produce a response with a significant increase observed at a concentration of about 1%.

EXAMPLE 3

Effect of Other Pluronic® Copolymers on Protein Expresion

Pluronic® copolymers are comprised of different lengths of hydrophilic (ethylene oxide (EO)) and hydrophobic (propylene oxide (PO)) blocks (Lemieux et al. (2000) Gene Ther., 7:986-991; Liaw et al. (2001) Gene Ther., 8:999-1004; Alakhov et al. (2001) Expert Opin. Biol. Ther., 1:583-602; Gebhart et al. (2003) Controlled Release Society, Glasgow, Scotland, UK; Pitard et al. (2002) Human Gene Ther., 13:1767-1775). The Pluronics® L35, L61, L64, F88, P85, P103, P123, F127, and a 1:8 mixture of Pluronic® L61 and Pluronic® F127 (Lemieux et al. (2000) Gene Ther., 7:986-991; Alakhov et al. (1999) Colloids Surfaces B: Biointerfaces, 16:113-134) were tested for their ability to increase production of luciferase as described in Example 1. The Pluronic® copolymers were tested at a concentration of 0.3%.

Of the tested Pluronic® copolymers, the copolymers with intermediate HLB values (i.e., 9-16) and a relatively large hydrophobic block (30-69 PO units), such as P123, P103, L64, and P85, were the most effective at increasing luciferase production (see, for example, FIG. 1 and FIGS. 5A and 5B). A 1:8 mixture of Pluronic® L61 and Pluronic® F127 (Lemieux et al. (2000) Gene Ther., 7:986-991; Alakhov et al. (1999) Colloids Surfaces B: Biointerfaces, 16:113-134), was also effective at increasing luciferase production (FIG. 5C). Hydrophilic Pluronics® F127 (HLB 22) and F88 (HLB 28); and Pluronics® comprising a relatively short PO block such as L35 (16 PO units) were effective at increasing luciferase production, but to a lesser extent than, for example, Pluronic® P85 (see, for example, FIG. 5D).

Notably, the pattern of the most active block copolymers observed is consistent with the increased potency of these copolymers to incorporate into the hydrophobic portions of cellular membranes, induce structural changes (e.g., membrane fluidization), and traverse the membrane to gain access to the cytosol (Batrakova et al. (2003) J. Pharmacol. Exp. Ther., 304:278-280).

EXAMPLE 4

Effects of Modification on Ability of Pluronic® P123 to Increase Protein Production Pluronic® P123 and polyethyleneimine (PEI) conjugated Pluronic® P123 (P123-PEI) have been previously optimized for the maximal expression of genes delivered in vitro and in vivo (Gebhart and Kabanov (2001) J. Contr. Release, 13:937-944; Nguyen et al. (2000) Gene Ther., 7:126-138; Ochietti et al. (2002) Gene Ther., 9:939-945; Gebhart et al. (2002) Bioconj. Chem., 13:937-944). P123-PEI was prepared as described in Nguyen et al. (Gene Ther. (2000) 7:126-138). Briefly, 0.5 mmol of 1,19-carbonyldiimidazole-activated P123 were reacted with 2.5 mmol of PEI, 2 kDa, in 30 ml of 0.2M carbonate buffer, pH 8.0. After 24 hours the reaction mixture was dialyzed twice and then lyophilized. The yield of PEI-P123 was 65%.

Pluronic® P123, PEI-P123, and a 9:1 (wt) mixture of Pluronic® P123 and PEI-P123 (P123/P123-PEI) were tested for their ability to increase production of luciferase as described in Example 1. As seen in Table 5, the P123/P123-PEI was the most effective at increasing production of luciferase, increasing the amount of expression almost 10-fold.

TABLE 5

| Formulation | Luciferase (pg/mg) |
| --- | --- |
| Media | 320 ± 14 |
| P123 (0.03%) | 545 ± 72* |
| P123-PEI (0.8 µM) | 650 ± 206 |
| P123/P123-PEI (0.8 µM) | 2823 ± 381 ** |

Values are mean ± SD (n = 3).
*= p < 0.05;
** = p < 0.005.

The effect of exogenous DNA added to the cells with Pluronics® P123 and P123-PEI was also studied. As seen in FIG. 6A, adding DNA (1 µg/ml) to the P123/P123-PEI caused the loss of the increased production of luciferase seen with the addition of P123/P123-PEI alone.

The effect of P123 and P123-PEI on global cellular protein expression was also investigated. As seen in FIG. 6B, P123 and P123-PEI, alone or in combination, were ineffective at increasing the total cellular protein levels present in cellular lysates. This result further suggests that the specificity of the polymers to increase expression from heterologous or foreign promoters.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for producing a protein comprising:
    a) providing cells comprising a heterologous nucleic acid encoding a recombinant protein; and
    b) incubating the cells in media containing at least one amphiphilic block copolymer,
    wherein said amphiphilic block copolymer comprises at least one block of poly(oxyethylene) and at least one block of poly(oxypropylene), and
    wherein said heterologous nucleic acid encoding a recombinant protein is controlled by a transcription element comprising a binding site for NF-κB or p53.

2. The method of claim 1, comprising the further step of:
    c) replacing said media containing an amphiphilic block copolymer with media lacking said amphiphilic block copolymer.

3. The method of claim 1, comprising the further step of isolating the expressed recombinant protein.

4. The method of claim 2, comprising the further step of isolating the expressed recombinant protein.

5. The method of claim 1, wherein said cells are mammalian cells.

6. The method of claim 1, wherein said amphiphilic block copolymer comprises a poly(oxyethylene)poly(oxypropylene)poly(oxyethylene) copolymer.

7. The method of claim 1, wherein said amphiphilic block copolymer has the formula:

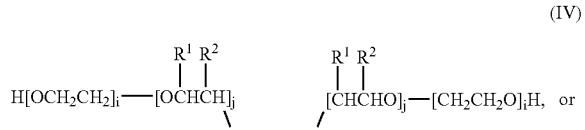
(IV)

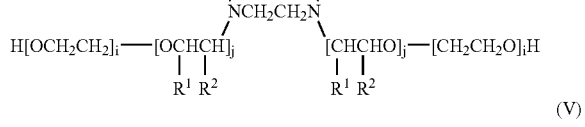
(V)

wherein i and j are independently from about 2 to about 800, and wherein each $R^1$, $R^2$ pair comprises one hydrogen and one methyl group.

8. The method of claim 1, wherein said amphiphilic block copolymer has a hydrophilic-lipophilic balance (HLB) of between 1 and 20.

9. The method of claim 8, wherein said amphiphilic block copolymer has an HLB of between 8 and 16.

10. The method of claim 6, wherein said amphiphilic block copolymer is selected from the group consisting of:

a) an amphiphilic block copolymer comprising approximately 39 oxyethylene units and approximately 69 oxypropylene units,
b) an amphiphilic block copolymer comprising approximately 39 oxyethylene units and approximately 60 oxypropylene units,
c) an amphiphilic block copolymer comprising approximately 52 oxyethylene units and approximately 40 oxypropylene units, and
d) an amphiphilic block copolymer comprising approximately 26 oxyethylene units and approximately 30 oxypropylene units.

11. The method of claim 1, wherein said at least one amphiphilic block copolymer is a mixture of different amphiphilic block copolymers.

12. The method of claim 1, wherein said amphiphilic block copolymer is a mixture of:
    a) a poly(oxyethylene)poly(oxypropylene)poly(oxyethylene) copolymer; and
    b) a polycation conjugated poly(oxyethylene)poly(oxypropylene)poly(oxyethylene) copolymer.

13. The method of claim 12, wherein said mixture comprises:
    a) a poly(oxyethylene)poly(oxypropylene)poly(oxyethylene) copolymer comprising approximately 39 oxyethylene units and approximately 69 oxypropylene units; and
    b) a polyethyleneimine conjugated poly(oxyethylene)poly(oxypropylene)poly(oxyethylene) copolymer comprising approximately 39 oxyethylene units and approximately 69 oxypropylene units.

14. The method of claim 13, wherein the ratio of the poly(oxyethylene)poly(oxypropylene)poly(oxyethylene) copolymer to the polyethyleneimine conjugated poly(oxyethylene)poly(oxypropylene)poly(oxyethylene) copolymer in said mixture is 9:1 by weight.

15. The method of claim 1, wherein said incubation of the cells in media comprising at least one amphiphilic block copolymer is for at least three hours.

16. The method of claim 15, wherein said incubation is for at least nine hours.

17. The method of claim 1, wherein said amphiphilic block copolymer is present in the media at a concentration ranging from about 0.0001% to about 5%.

18. The method of claim 17, wherein said concentration ranges from about 0.1% to about 2%.

19. The method of claim 1, wherein said heterologous nucleic acid is stably incorporated into said cells.

20. The method of claim 1, wherein said heterologous nucleic acid encoding a recombinant protein is controlled by the cytomegalovirus promoter.

21. The method of claim 1, wherein said recombinant protein is selected from the group consisting of cytokines, enzymes, clotting factors, vaccines, antibodies, growth factors and hormones, insulin, hemoglobin, alpha-1-antitrypsin (AAT), lactoferrin, cystic fibrosis transmembrane conductase (CFTR), human protein C, anti-viral agents, and interleukins.

22. The method of claim 21, wherein said recombinant protein is Factor VIII and said amphiphilic block copolymer has a hydrophilic-lipophilic balance (HLB) of between 1 and 20.

23. A method for producing a protein in a host comprising:
    a) providing a cell comprising a heterologous nucleic acid encoding a recombinant protein;
    b) incubating the cells in media containing at least one amphiphilic block copolymer; and
    c) introducing the cells into a host, wherein said amphiphilic block copolymer comprises at least one block of poly(oxyethylene) and at least one block of poly(oxypropylene), and wherein said heterologous nucleic acid encoding a recombinant protein is controlled by a transcription element comprising a binding site for NF-κB or p53.

24. The method of claim 23, wherein the cells in step a) are obtained from the host and the heterologous nucleic acid was subsequently incorporated into the cells in vitro.

25. A method for enhancing production an RNA comprising:
   a) providing cells comprising a heterologous DNA encoding an RNA; and
   b) incubating the cells in media containing at least one amphiphilic block copolymer, wherein said amphiphilic block copolymer comprises at least one block of poly(oxyethylene) and at least one block of poly(oxypropylene), and wherein said heterologous nucleic acid encoding a recombinant protein is controlled by a transcription element comprising a binding site for NF-κB or p53.

26. The method of claim 25, wherein said encoded for RNA is an siRNA.

27. The method of claim 25, wherein said heterologous nucleic acid encoding a recombinant protein is controlled by the cytomegalovirus promoter or a polymerase III promoter.

* * * * *